United States Patent [19]
Eldred

[11] Patent Number: 5,118,296
[45] Date of Patent: Jun. 2, 1992

[54] DENTAL RESTORATION AND METHOD OF MANUFACTURING

[76] Inventor: Peter Eldred, P.O. Box 283G, Otego, N.Y. 13825

[21] Appl. No.: 565,222

[22] Filed: Aug. 9, 1990

Related U.S. Application Data

[63] Continuation-in-part of Ser. No. 364,254, Jun. 9, 1989, abandoned.

[51] Int. Cl.$^5$ ............................................. A61C 5/10
[52] U.S. Cl. .................................... 433/223; 433/208; 433/218
[58] Field of Search ............ 433/223, 208, 206, 212.1, 433/222.1, 218, 201.1, 228.1

[56] References Cited

U.S. PATENT DOCUMENTS

| | | | |
|---|---|---|---|
| 2,930,125 | 3/1960 | Pos | 433/223 |
| 3,423,831 | 1/1969 | Semmelman | 433/212.1 |
| 4,292,029 | 9/1981 | Craig et al. | 433/228.1 |
| 4,895,516 | 1/1990 | Hulten | 433/201.1 |

*Primary Examiner*—John J. Wilson
*Attorney, Agent, or Firm*—Thomas A. O'Rourke

[57] ABSTRACT

In the formation of a dental restoration unit, a procedure for securely bonding composite resin material to a core structure is employed. A core structure comprising, for example, metal, is wholly or partially covered with a cohesion layer comprised of a blend of lithium, aluminum silicat and fused quartz silicate. The composite resin material is fused to the cohesion. The resulting restoration unit, such as a crown, is less liable to fracture than is porcelain, and can provide a surface which is no more abrasive than is natural tooth enamel.

17 Claims, 1 Drawing Sheet

DENTAL RESTORATION AND METHOD OF MANUFACTURING

This application is a continuation-in-part of U.S. application Ser. No. 07/364,254 filed on Jun. 9, 1989, now abandoned, the disclosures of which are incorporated herein by reference.

BACKGROUND OF THE INVENTION

1. Field of the Invention

Although the dental profession has made great strides in alerting the public about the need for regular dental examinations and the profession, through fluoride treatment and improved dental hygiene has lessened the risk of dental caries, many people are still in need of major dental reconstruction. Where, due to illness or poor routine care a tooth has become seriously decayed or through accident a tooth has become damaged, there is still a significant need for tooth reconstruction.

While in past years there may have been a tendency to completely remove a damaged tooth, more modern dental procedure believes that as much of the natural tooth as possible should be saved and preferable repaired. Thus, when the root of the tooth has become exposed through for example serious decay, rather than pulling the tooth, the dentist will attempt to remove as much of the caries as possible. The dentist may also perform root canal treatment on the tooth as part of the treatment. Once the treatment of the decay and/or root damage has been completed, reconstruction of the tooth surface must begin. Then, using various materials, a tooth must be re-formed to provide many years of useful life.

This invention relates generally to the manufacture of artificial tooth reconstructions and more particularly to the application of composite resin to a metal base by means of a superior cohesion layer.

2. Description of the Prior Art

Dental reconstructions comprising a metal base covered with a layer of porcelain are well known. In fact, the use of porcelain in dental reconstruction dates back several hundred years.

However, the porcelain that is used is very abrasive to natural tooth enamel and can cause destruction of the enamel of the teeth opposing the reconstructed surface.

Dentists have found that existing periodontal disease can be aggravated by opposing porcelain dentition. In addition, a porcelain restoration can aggravate peridontal disease associated with the reconstructed tooth. This occurs because the porcelain does not absorb any of the stress produced by action of the opposing dentition against the reconstructed tooth. Another problem associated with porcelain is its tendency to fracture under stress.

Attempts to improve the use of porcelain in teeth have included porcelain fused to metal restorations whereby a particulate suspension of porcelain is applied to a metal alloy. The porcelain is fired in an appropriate furnace and the porcelain is vitrified to the alloy. Porcelain is applied in several layers to achieve the proper appearance so that the restoration matches the other teeth in color.

More recently, there was described in U.S. Pat. No. 4,895,516, the disclosures of which are incorporated herein by reference, a method of manufacturing a resin alloy substructure reinforced dental restoration. The method includes coating the crown and bridge alloy substructure with a porcelain or vitrifiable ceramic. The ceramic is vitrified to fuse the ceramic to the substructure which forms a bonding layer on the substructure. A microporous surface on the ceramic bonding layer is formed with an etching material and thereupon a silane coupling agent is applied to the microporous layer. A polymerizable resin or a composite resin material is placed over the silane coupling agent. Finally, the resin or composite resin material is polymerized.

While such a method may be an improvement over prior methods, it has been found that a superior restoration may be obtained in accordance with the present invention. The present invention eliminates the need for an etching step followed by the use of a silane coupling agent by providing an improved cohesion layer that is absorbent.

Other prior art patents include U.S. Pat. No. 4,654,007 to Sigler and 3,423,831 to Semmelman, the disclosures of which are incorporated herein by reference.

A principal object of the invention is to provide an improved method for securely affixing a composite resin material to the metal base of a reconstruction or crown.

Another object of the invention is to provide a strong chemical bond between the composite resin material and the alloy surface.

Another object of the invention is to provide a dental reconstruction unit or crown which comprises a composite resin material securely bonded to a metal base by means of an intermediate layer, made from the composition of the present invention, such reconstruction unit or crown being more durable and less abrasive than previous units or crowns.

The invention consists of the novel combinations, steps, processes and improvements herein shown and described.

DESCRIPTION OF THE PREFERRED EMBODIMENTS

Figure 1:
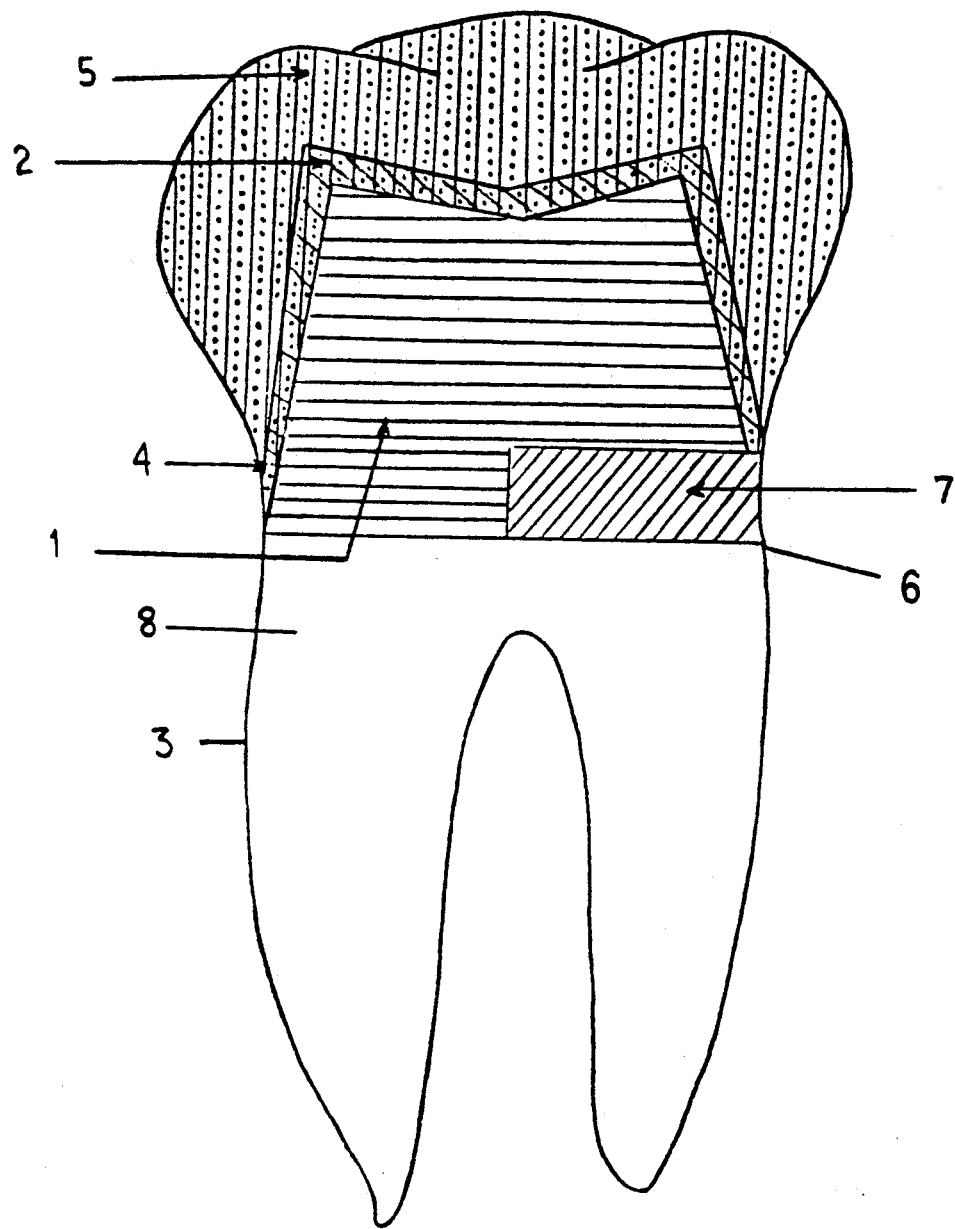
FIG. 1 is a cross-section drawing of a tooth restored using the method of the present invention.

Generally, the initial steps in the process of preparing a dental restoration unit take place in the dentist's office. A negative impression, and optionally a positive impression of the patient's teeth, is made and sent to the dental lab. At the dental lab the technician performs the preparative steps familiar to those skilled in the art. The restorations of the present invention are those typically known in the industry and include but are not limited to jackets, inlays and onlays.

In accordance with the principles of the present invention, a metal core or coping is prepared. This core is waxed, invested, cast and finished using conventional techniques. The metal may be any metal capable of withstanding the high temperatures needed for firing the porcelain. One suitable metal is Aurium Surefire. A semi-precious metal sold by Aurium Research Corporation, 130 County Courthouse Road, Garden City Park, N.Y., 11040. The exterior surface of the metal is preferably finished with 200 mesh aluminum oxide discs and steamed cleaned.

The preferred cohesion layer of the present invention is a compound formed by combining, in powdered form lithium, aluminum silicate and a fused quartz silicate. The mixture is then mixed with distilled water to form a low viscosity paste. The preferred ratio provides a consistency which can be applied to the metal core with a small brush.

The metal core with the cohesion layer thereon is placed in front of the muffle of a porcelain firing furnace and pre-heated to 1000 degrees. Then, the restoration is placed in the oven and heated at a rate of 100 degrees F. per minute. When the oven reaches 1750 degrees F. the restoration is removed from the oven and cooled to room temperature. The heating of the cohesion layer by the furnace fuses it to the metal core.

Unlike the porcelain opaque of the prior art, the cohesion layer of the present invention is relatively absorbent and it is therefore unnecessary to etch the cohesion layer as is the case with a porcelain opaque to create a strong bond. An absorbent procelain opaque which has sufficient absorbency to avoid the need to etch the porcelain opaque with an etching acid to obtain micropore as required by a prior art is also included in this invention. This absorbent procelain opaque is obtained by heating the porcelain opaque to a temperature just above the glass transition temperature. This heating adheres the porcelain opaque to the coping but retains absorbency for adhering the bonding layer thereto. Thus, the acid etch is unnecessary.

The composition of the dry mixture for the cohesion layer is preferably about 25% to about 75% fused quartz silicate. More preferably, about 40% to about 60% fused quartz silicate and most preferably 50% fused quartz silicate are other compositions of the mixture. The lithium and aluminum silicate is generally sold as a mixture under the name of Jelenko Glaze and blended with the fused quartz silicate.

Once the cohesion layer has been fired, a thin layer of light polymerized bonding liquid is painted over the entire surface. The bonding liquid is preferably ESPE Visio Gem available from ESPE - Premier Sales Corp. P.O. Box 111, Norristown, Pa. 19904. Because the cohesion layer is absorbent, the bonding layer is absorbed into the cohesion layer. The assembly is then cured under a U.V. source for about 60 seconds. The UV source is preferably a VISIO Gem Alpha curing light. Alternative bonding liquids include dental cements such as zinc phosphate cement, and glass ionomer. The cements preferably have a low viscoity.

The restoration is built up with a composite resin material using filled or unfilled composite resin. For example, a composite resin of a particular shade, such as body, translucent or incisor, can be used to match the coloring of the patient's teeth. In building-up the restoration a preferred composite resin is a white micro filled composite resin such as ESPE Visio Gem brand light activated composite. The unit is cured in the absence of oxygen, under vacuum for 15 minutes to permit final polymerization. Curing in the absence of oxygen prevents the formation of a smear layer which is often observed with cross linked resins.

In the final steps, the cured restoration unit is shaped and contoured, then polished. The unit is then ready to be sent to the dentist for placement in the patient's mouth.

In another embodiment of the present invention in place of the metal core or coping a temporary coping is used. This coping may be a platinum foil or other suitable metal foil which acts like a matrix and is applied to a die usually a stone die. The foil takes on the shape of the preparation in the die. The cohesion layer is painted on the foil once it is removed from the die. The cohesion layer is fired in the oven as described above. The light polymerized bonding layer adhesive is painted over the surface of the cohesion layer. Porcelain or composite is applied to the bonding layer as described above. Once the restoration has been built up the foil is removed and adhesive is applied and the restoration is inserted into the mouth.

It has been found that dental restorations comprising composite resin and the cohesion layer can withstand stresses of opposing dentition that would fracture restorations composed solely of porcelain opaque fused to metal. The composite resin layer absorbs some of the force from the opposing dentition and is less likely to cause further damage to periodontal disease of the opposing dentition o the reconstructed tooth.

The following is an illustrative example of the present invention. It is to be understood however, that the example is presented for purposes of illustration only, and nothing therein is to be taken as a limitation upon the overall scope of the invention. While construction of a crown is specifically described, it will be appreciated that the invention is not limited to this type of procedure, but rather pertains to virtually any restoration including inlays, onlays, full crown overlays or jackets. Moreover, preferred techniques described can be modified in respects as the need arises without departing from the principles of the invention.

EXAMPLE

The following example sets forth the procedures in accordance with the present invention. This example is given with reference to the accompanying drawing in order to facilitate a complete understanding of the invention.

In the first step, a metal core or base, 1, is waxed, invested, cast and finished using techniques known in the art. The metal may be any metal capable of fusing with the cohesion layer and withstanding the high temperatures used for firing the unit. The exterior surface of the coping is finished with aluminum oxide discs and steam cleaned. It is preferable to use Centrex brand aluminum oxide discs for this procedure. (Such discs are available from Dentsply Company, York, Pa. 17405). Finally, the cohesion layer, 2, is applied to sufficiently mask the metal, as described above. If desired a small portion of metal may be left uncovered to form a collar, 7, near the margin, 6, where the edge of the crown meets the tooth 3. The unit is fired to fuse the cohesion layer to the metal. A thin layer of bonding liquid, 4, is painted over the entire cohesion layer opaque surface to just wet the surface. The unit is then cured under a U.V. for 60 seconds source.

Finally, the restoration is built up with a composite material, 5, filled or unfilled, such as ESPE Visio Gem brand light activated composite. Composite material in the various shades, for example, body, incisor and translucent, can be used. The unit is then cured under vacuu to allow final polymerization in the absence of oxygen, such as in a Visio Gem Beta vacuum curing unit, for 15 minutes. In the third step, the cured restoration is first shaped and contoured using burrs and a small white rubber wheel (preferably Dedeco Brand available from Dedeco Int., Inc., Long Eddy, N.Y. 12760). The unit is then polished with a white buffing compound on a small muslin buff wheel at slow speed. Alternatively, a diamond porcelain polishing compound can be used with a small felt wheel at a very low speed (e.g. 300 RPM).

Next, the internal surface is sandblasted for a few seconds with 60 micron aluminum oxide sand. If the unit has a metal collar 7 above the margin 6, the metal collar is polished. The unit is then ready to be placed in the patient's mouth by a dentist. The restoration is placed on the natural tooth structure (9-14) immediately over the dentin layer, 8. Often the reconstructed tooth will be affected by periodontal disease, and the composite resin absorbs some of the stress from opposing dentition, thus limiting the secondary occlusal trauma. In addition, periodontal disease of the opposing dentition will also be less subject to secondary occlusal trauma. Another benefit of the composite resin is its ability to withstand stresses that could fracture prior art/metal restorations.

One of the benefits of the use of the cohesion layer of the present invention is that it avoids the need for using a porcelain opaque. By not using the porcelain opaque there is, therefore, no necessity for etching the porcelain opaque or applying a silane coupling agent and forming microfissures in the porcelain opaque surface to promote bonding.

Those skilled in the art will appreciate that a number of variations and changes can be made in the preferred method hereof without departing from the spirit and scope of the invention. Such changes may include differences in specific method steps and/or materials, so long as the essentials of the invention are satisfied. It is, of course, intended to cover all such variations and changes within the scope of the invention.

What is claimed is:

1. A method of manufacturing a tooth reconstruction comprising bonding a composite resin to a coping by means of an absorbent cohension layer, said absorbent cohension layer being formed by combining lithiu, aluminum silicate and a fused quartz silicate, mixing said mixture with water to form a paste, applying the paste to the coping, heating the coping to fuse the cohesion layer to the metal core whereby said cohesion layer after heating is sufficiently absorbent to be capable of receiving an adhesive without etching the surface of the cohesion layer.

2. A method according to claim 1 wherein the coping with the cohesion layer thereon is preheated to 1000 degrees F. and then heated at a rate of 100 degrees F. per minute until the oven reaches 1750 degrees F.

3. A method according to claim 2 wherein said adhesive is a light polymerized bonding liquid.

4. The method of claim 3 wherein the cohesion layer comprises about 25% to about 75% fused quartz.

5. The method of claim 4 wherein the cohesion layer comprises about 40% to about 60% fused quartz silicate.

6. The method of claim 3 in which the coping structure comprises a metal.

7. The method of claim 3 in which the composite resin comprises a material having an abrasive factor less than that of porcelain.

8. The method of claim 3 in which the composite resin comprises a material having an abrasive factor no greater than that of natural tooth enamel.

9. A method of manufacturing a tooth reconstructions comprising.
   1) providing a coping;
   2) applying an absorbent cohesion layer of powdered lithium, aluminum silicate and a fused quartz silicate, mixing with water to form a paste;
   3) heating the coping to fuse the cohension layer to the metal core and thereby forming an cohesion layer that is absorbent without etching;
   4) applying a thin layer of adhesive which is capable of being absorbed by said cohesion layer;
   5) curing said adhesive;
   6) applying an outer covering selected from the group consisting of a composite resin or porcelain.

10. A method according to claim 9 wherein said cohesion layer comprises a blend of lithium, aluminum silicate and fused quartz.

11. A method according to claim 9 wherein said cohesion layer comprises a porcelain opaque and said cohesion layer is heated to just about its glass transition temperature.

12. A method according to claim 9 wherein said adhesive is a light polymerized bonding liquid.

13. A dental restoration unit comprising a coping having applied thereto an absorbent cohesion layer formed by applying a paste made from a powder of lithium, aluminum silicate and a fused quartz silicate mixed with water and wherein the coping bearing said cohesion layer has been heated to a form surface that is absorbent in the absence of etching.

14. The dental restoration unit of claim 13 wherein said coping is a metal core supporting said inner layer.

15. The dental restoration unit of claim 14 wherein said blend comprises about 40% to about 60% fused quartz.

16. The dental restoration unit of claim 15 wherein said blend comprises about 40% to about 60% fused quartz silicate.

17. The dental restoration unit of claim 13 in which the composite resin comprises a material having an abrasive factor no greater than that of natural tooth enamel.

* * * * *